United States Patent [19]

Seybold

[11] Patent Number: 4,560,751
[45] Date of Patent: Dec. 24, 1985

[54] PREPARATION OF N,N-DISUBSTITUTED 2-AMINOTHIAZOLES

[75] Inventor: Guenther Seybold, Neuhofen, Fed. Rep. of Germany

[73] Assignee: BASF Aktiengesellschaft, Ludwigshafen, Fed. Rep. of Germany

[21] Appl. No.: 509,428

[22] Filed: Jun. 30, 1983

[30] Foreign Application Priority Data

Jul. 22, 1982 [DE] Fed. Rep. of Germany ....... 3227329

[51] Int. Cl.[4] .......................................... C07D 277/42
[52] U.S. Cl. ..................................... 544/60; 544/133; 544/367; 546/209; 548/184; 548/190; 548/191; 548/137; 564/23
[58] Field of Search ............... 548/190, 191, 184, 137; 544/60, 133, 367; 546/209

[56] References Cited

U.S. PATENT DOCUMENTS 3,775,425 11/1973 Bosshard .............................. 548/190

OTHER PUBLICATIONS

Viski et al., Acta Chim. Hung. 112, 323 (1983).
Hartmann et al., J. Prakt Chem. 320, 647 (1978).
Kutschy et al., Coll Czech Chem. Comm. 46, 436 (1980).

*Primary Examiner*—Robert Gerstl
*Attorney, Agent, or Firm*—Oblon, Fisher, Spivak, McClelland & Maier

[57] ABSTRACT

Compounds of the general formula I

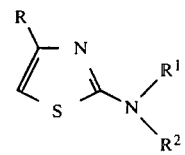

where R is unsubstituted or substituted alkyl, alkenyl, aryl or hetaryl and $R^1$ and $R^2$ independently of one another are each unsubstituted or substituted alkyl or aryl, or, together with the nitrogen, form a heterocyclic ring, are prepared by a process wherein a compound of the general formula II

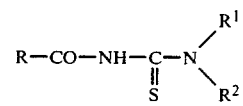

is reacted with a water-soluble monohaloacetate in an aqueous alkaline medium. They are very useful coupling components for the preparation of azo dyes.

14 Claims, No Drawings

PREPARATION OF N,N-DISUBSTITUTED 2-AMINOTHIAZOLES

The present invention relates to a process for the preparation of compounds of the general formula I

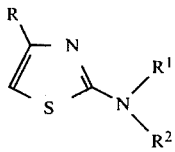

where R is unsubstituted or substituted alkyl, alkenyl, aryl or hetaryl and $R^1$ and $R^2$ independently of one another are each unsubstituted or substituted alkyl or aryl, or, together with the nitrogen, form a heterocyclic ring, wherein a compound of the general formula II

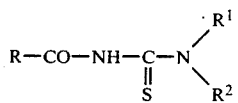

is reacted with a water-soluble monohaloacetate in an aqueous alkaline medium.

Alkyl radicals R are of, for example, 1 to 10 carbon atoms and can be substituted by, for example, fluorine, chlorine, bromine, hydroxyl, $C_1$-$C_4$-alkoxy, $C_1$-$C_4$-alkylmercapto, phenoxy, phenylmercapto, nitro, $C_2$-$C_4$-alkanoylamino, $C_1$-$C_4$-dialkylamino, aryl or hetaryl.

Alkenyl is preferably of not more than 4 carbon atoms.

Specific examples of radicals are $CH_3$, $C_2H_5$, $C_3H_7$, $C_4H_9$, $C_5H_{11}$, $C_6H_{13}$, $C_7H_{15}$, $CH_2CH=CH_2$, $CH_1-CH=CH-CH_3$, $CH_2C_6H_5$, $CH_2Cl$, $C_2H_4Cl$, $CH_2OH$, $CH_2N(CH_3)_2$, $C_2H_4N(CH_3)_2$, $CH_2OCH_3$, $CH_2OC_2H_5$, $CH_2SCH_3$, $CH_2SC_2H_5$, $CH_2SC_6H_5$, $CH_2NHCOCH_3$,

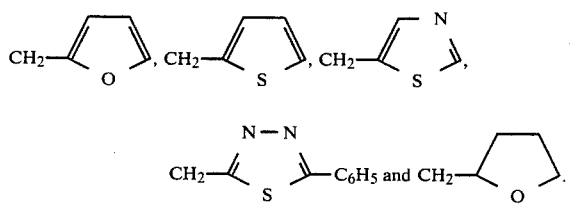

Aryl radicals R are, for example, naphthyl or phenyl which is monosubstituted or polysubstituted by $C_1$-$C_8$-alkyl, $C_1$-$C_4$-alkoxy, dialkylamino, β-cyanoethoxy, β-$C_1$-$C_8$-alkoxycarbonylethoxy, $C_1$-$C_4$-alkylmercapto, phenylmercapto, chlorine, bromine, nitro or $C_1$-$C_4$-alkanoylamino, such as acetylamino, propionylamino or butyrylamino.

Specific examples of radicals R are: $C_6H_5$, $C_6H_4Cl$, $C_6H_4Br$, $C_6H_4CH_3$, $C_6H_3ClCH_3$, $C_6H_4NO_2$, $C_6H_3ClNO_2$, $C_6H_4OCH_3$, $C_6H_4OC_2H_5$, $C_6H_4OC_6H_5$, $C_6H_3(OCH_3)_2$, $C_6H_3(CH_3)_2$, $C_6H_2(OCH_3)_3$, $C_6H_4N(CH_3)_2$, $C_6H_4N(C_2H_5)_2$, $C_6H_4C_4H_9$, $C_{10}H_7$,

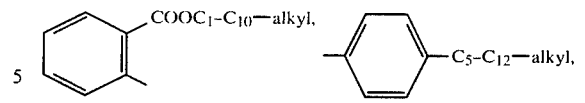

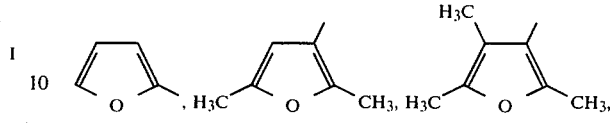

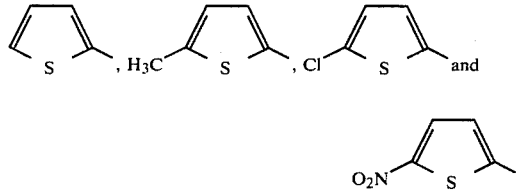

$R^1$ and $R^2$ are each, for example, $C_1$-$C_8$-alkyl which can furthermore be interrupted by oxygen and substituted by hydroxyl, cyano, chlorine, $C_1$-$C_4$-alkoxy, $C_1$-$C_4$-alkanoyloxy, $C_1$-$C_4$-alkoxycarbonyl, $C_1$-$C_4$-alkanoylamino, acetyl, $C_1$-$C_4$-alkylaminocarbonyloxy, arylaminocarbonyloxy, $C_1$-$C_4$-alkoxycarbonyloxy or phenoxycarbonyloxy, or are each allyl, methallyl, propargyl, cyclohexyl, phenyl-$C_1$-$C_5$-alkyl, phenoxyethoxypropyl, phenyl, methoxyphenyl, ethoxyphenyl or tolyl.

Specific examples of radicals in addition to those mentioned above are methyl, ethyl, propyl, butyl, β-hydroxyethyl, β-methoxyethyl, γ-methoxypropyl, β-cyanoethyl, β-carbomethoxyethyl, β-carboethoxyethyl, β-acetoxyethyl, β-ethoxycarbonylethyl, γ-acetylaminopropyl, phenoxycarbonyloxyethyl, butylaminocarbonyloxyethyl, benzyl and β-phenylethyl.

$R^1$ and $R^2$ together with the nitrogen are, for example, pyrrolidino, piperidino, morpholino, piperazino, α-methylpiperazino, hexamethyleneimino or thiomorpholino S-dioxide.

An advantageous method of carrying out the novel process is to heat the compound of the formula II with an equimolar or larger amount (not more than ~1.5 moles) of the haloacetate in an aqueous alkaline solution for from 3 to 8, preferably from 4 to 6, hours at from 50° to 110° C., preferably from 80° to 95° C.

The compounds of the formula I separate out as a rule in the form of oils and can be isolated in a conventional manner, for example by extraction, phase separation or distillation.

Examples of suitable haloacetates are water-soluble alkaline earth metal and ammonium salts and in particular alkali metal salts, of which the Na salt is preferred. An example of a suitable aqueous alkaline medium is dilute sodium hydroxide solution (about 3–15% strength). Instead of using the monohaloacetate, it is possible in many cases to employ the corresponding acid and produce the salt in situ by adding the base.

In a particularly preferred embodiment of the novel process, the compound of the formula II is prepared by reacting an acid halide of the formula

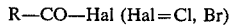

R—CO—Hal (Hal=Cl, Br)

with an alkali metal thiocyanate or ammonium thiocyanate in a solvent, such as acetone, acetonitrile or cyclohexanone, and then adding an amine of the formula

after which water, the alkali and the monohaloacetate are added and the solvent is removed, the compound of the formula II not being isolated in this process.

In the Examples which follow, and illustrate the preparation, parts and percentages are by weight, unless stated otherwise.

The compounds of the formula I are useful intermediates for the preparation of dyes; for example, they are suitable coupling components, cf. for example German Laid-Open Application DOS No. 2,816,505 or European Pat. No. 17,769.

A process for the preparation of thiazoles is disclosed in East German Pat. No. 112,760, but this process does not give thiazoles which are unsubstituted in the 5-position.

EXAMPLE 1

16.86 parts of benzoyl chloride are added dropwise to a thoroughly stirred mixture of 15 parts of acetone and 9.75 parts of sodium thiocyanate at 20°–30° C. in the course of 60–90 minutes while cooling with water, and the mixture is then stirred for one hour at room temperature. Thereafter, 9.63 parts of diethylamine are added dropwise in the course of 60–90 minutes, while cooling with water, the addition being carried out in such a manner that the temperature does not exceed 40° C. Stirring is then continued for 2 hours at 40° C., and the mixture is diluted with 45 parts of water. 13.62 parts of chloroacetic acid and 21 parts of 50% strength sodium hydroxide solution are added to the reaction solution, the temperature increasing to 50°–60° C. during the addition. The mixture is then slowly heated at 90°–95° C., 10–12 parts of an acetone/water mixture being distilled off. The mixture is stirred at this temperature for 12 hours, after which it is cooled to 70°–75° C., and the aqueous (lower) phase is drawn off and the upper, oily phase is removed. Yield: 24.5 parts (≃80% of theory) of 2-diethylamino-4-phenylthiazole.

EXAMPLE 2

774 parts of crude p-methoxybenzoyl chloride (calculated as 100%) are added dropwise to a thoroughly stirred mixture of 700 parts of acetone and 374 parts of sodium thiocyanate at 20°–30° C. in the course of 60–90 minutes while cooling with water, and the mixture is then stirred for one hour at room temperature. Thereafter, 370 parts of diethylamine are added dropwise in the course of 60–90 minutes, while cooling with water, the addition being carried out in such a manner that the temperature does not exceed 40° C. Stirring is then continued for 2 hours at 40° C., and the mixture is diluted with 1,725 parts of water. 522 parts of chloroacetic acid and 800 parts of 50% strength sodium hydroxide solution are added to the reaction solution, the temperature increasing to 50°–60° C. during the addition. The mixture is then slowly heated to an internal temperature of 90°–95° C., an acetone/water mixture being distilled off. The mixture is stirred at this temperature for 12 hours, after which it is cooled to 70°–80° C., and the aqueous (lower) phase is drawn off at this temperature and the desired oily product is removed. Yield: 1,093 parts (≃88% of theory) of 2-diethylamino-4-p-methoxyphenylthiazole; 96% pure according to gas chromatography.

EXAMPLE 3

562 parts of benzoyl chloride are added dropwise to a thoroughly stirred mixture of 500 parts of acetone and 324 parts of sodium thiocyanate at 20°–30° C. in the course of 1–1.5 hours, while cooling with water, and the mixture is then stirred for a further half hour at room temperature. Thereafter, 404 parts of N-butyl-N-ethylamine are added dropwise at 20°–30° C., while cooling with water, the mixture is stirred vigorously for a further 2 hours at room temperature, 1,000 parts of water are added and the mixture is stirred up for a short time. The aqueous (lower) phase is then drawn off and 1,000 parts of water and 454 parts of chloroacetic acid are added. 640 parts of 50% strength sodium hydroxide solution are then run in, the temperature increasing to 50°–60° C. during this procedure. The mixture is then refluxed, and an acetone/water mixture is distilled off until the internal temperature has increased to 90° C. (about 200 parts). The mixture is kept at this temperature for 6–8 hours, after which it is cooled, the aqueous (lower) phase is drawn off and the product is removed. Yield: 1,109 parts of a yellowish oil which according to gas chromatographic analysis contains 840 parts (≃81% of theory) of 2-N-ethyl-N-butylamino-4-phenylthiazole.

EXAMPLE 4

116.8 parts of thiophene-2-carboxylic acid chloride are added dropwise to a vigorously stirred mixture of 66.4 parts of sodium thiocyanate and 126 parts of acetone at from −5° to 0° C. in the course of 1 hour. Stirring is then continued for 30 minutes at 0° C., and 60 parts of diethylamine are added dropwise in the course of 1–1.5 hours at from −2° to +2° C. Stirring is continued for a further hour at 0° C. and for 30 minutes at 5°–10° C., after which 320 parts of water, 83 parts of chloroacetic acid and 135 parts of 50% strength NaOH are added and the mixture is slowly heated to 90° C., acetone being distilled off. The mixture is stirred for a further 4 hours at 90°–95° C., after which it is cooled, and the product is separated off as the upper oily phase, at 70° C. Yield: 170 parts of crude product=153 parts (≃80% of theory) of 4-thienyl-2-diethylaminothiazole.

The compounds below are prepared by a method similar to that described in Example 1.

| Example | Acid chloride | Amine | Thiazole |
|---|---|---|---|
| 5 | ![furan-COCl with H3C-O-CH3] | HNEt$_2$ | ![thiazole product H3C-O-CH3-S-NEt2] |

-continued

| Example | Acid chloride | Amine | Thiazole | |
|---|---|---|---|---|
| 6 | ![furan-COCl] | HNEt₂ | 2-furyl thiazole with NEt₂ | |
| 7 | 2,5-dimethyl-3-COCl furan (with H₃C groups) | HNEt₂ | corresponding thiazole with NEt₂ | |
| 8 | 4-O₂N-C₆H₄-COCl | HN(C₄H₉)₂ | 4-nitrophenyl thiazole with N(C₄H₉)₂ | m.p. 76° C. |
| 9 | 4-(H₃C)₂N-C₆H₄-COCl | HN(C₂H₅)₂ | 4-dimethylaminophenyl thiazole with N(C₂H₅)₂ | m.p. 90–92° C. |
| 10 | 4-(H₃C)₂N-C₆H₄-COCl | HN(CH₂—CH=CH₂)₂ | 4-dimethylaminophenyl thiazole with N(C₃H₅)₂ | |
| 11 | 3,4,5-(CH₃O)₃-C₆H₂-COCl | HN(C₂H₅)₂ | 3,4,5-trimethoxyphenyl thiazole with N(C₂H₅)₂ | m.p. 112° C. |
| 12 | (CH₃)₃C—COCl | HN(C₂H₅)₂ | (CH₃)₃C- thiazole with N(C₂H₅)₂ | |
| 13 | " | HN(CH₃)₂ | (CH₃)₃C- thiazole with N(CH₃)₂ | |
| 14 | (CH₃)₂CH—COCl | HN(C₂H₅)₂ | (CH₃)₂CH- thiazole with N(C₂H₅)₂ | |
| 15 | C₆H₅CH₂—COCl | HN(C₄H₉)₂ | C₆H₅CH₂- thiazole with N(C₄H₉)₂ | |
| 16 | C₂H₅O—CH₂—COCl | HN(C₂H₅)₂ | C₂H₅O—CH₂- thiazole with N(C₂H₅)₂ | |

-continued

| Example | Acid chloride | Amine | Thiazole |
|---|---|---|---|
| 17 | $C_4H_9\text{-CH(C}_2H_5\text{)-COCl}$ | $HN(C_2H_5)_2$ | $C_4H_9\text{-CH(C}_2H_5\text{)-CH=thiazole-}N(C_2H_5)_2$ |
| 18 | $CH_3\text{-}S\text{-}CH_2\text{-}CH_2COCl$ | morpholine (HN-O) | $CH_3S\text{-}CH_2\text{-}CH_2$-thiazole-morpholine |
| 19 | $C_6H_5\text{-}CH=CH\text{-}COCl$ | $HN(C_2H_5)_2$ | $C_6H_5\text{-}CH=CH$-thiazole-$N(C_2H_5)_2$ |
| 20 | thienyl-$CH_2COCl$ | " | thienyl-$CH_2$-thiazole-$N(C_2H_5)_2$ |
| 21 | $H_5C_6$-thiadiazole-$CH_2COCl$ | " | $H_5C_6$-thiadiazole-$CH_2$-thiazole-$N(C_2H_5)_2$ |

I claim:

1. A process for the preparation of an N,N-disubstituted 2-aminothiazole of the formula I

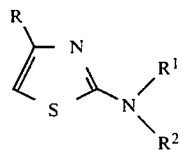

where R is an alkyl group of 1 to 10 carbon atoms which may be substituted by fluorine, chlorine, bromine, hydroxyl, $C_1$-$C_4$-alkoxy, $C_1$-$C_4$-alkylmercapto, phenoxy, phenylmercapto, nitro, $C_2$-$C_4$-alkanoylamino, $C_1$-$C_4$-dialkylamino, phenyl,

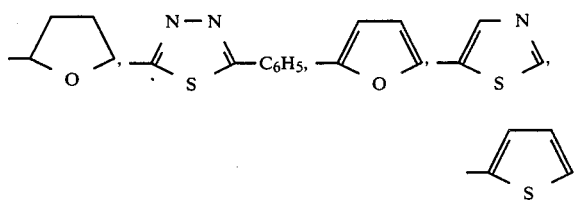

or an aryl radical which is naphthyl or phenyl which is monosubstituted or polysubstituted by $C_1$-$C_8$-alkyl, $C_1$-$C_4$ alkoxy, dialkylamino, $\beta$-cyanoethoxy, $\beta$-$C_1$-$C_8$-alkoxycarbonylethoxy, $C_1$-$C_4$-alkylmercapto, phenylmercapto, chlorine, bromine, nitro or $C_1$-$C_4$-alkanoylamino, and $R^1$ and $R^2$ are each $C_1$-$C_8$-alkyl which can be interrupted by oxygen or substituted by hydroxyl, cyano, chlorine, $C_1$-$C_4$-alkoxy, $C_1$-$C_4$-alkanoyloxy, $C_1$-$C_4$-alkoxycarbonyl, $C_1$-$C_4$-alkanoylamino, acetyl, $C_1$-$C_4$-alkylaminocarbonyloxy, arylaminocarbonyloxy, $C_1$-$C_4$-alkoxycarbonyloxy, or phenoxycarbonyloxy, or are each allyl, methallyl, propargyl, cyclohexyl, phenyl-$C_1$-$C_5$-alkyl, phenoxyethoxypropyl, phenyl, methoxyphenyl, ethoxyphenyl or tolyl, or $R^1$ and $R^2$ together with a nitrogen are pyrrolidino, piperidino, morpholino, piperazino, $\alpha$-methylpiperazino, hexamethyleneimino or thiomorpholino S-dioxide, wherein a compound of the formula II

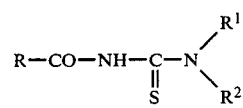

where R, $R^1$ and $R^2$ are defined as in formula I, is reacted with a water-soluble monohaloacetate in an aqueous alkaline medium.

2. The process of claim 1, wherein R is $CH_3$, $C_2H_5$, $C_3H_7$, $C_4H_9$, $C_5H_{11}$, $C_6H_{13}$, $C_7H_{15}$, $CH_2CH=CH_2$, $CH_2$—$CH=CH$—$CH_3$, $CH_2C_6H_5$, $CH_2Cl$, $C_2H_4Cl$, $CH_2OH$, $CH_2N(CH_3)_2$, $C_2H_4N(CH_3)_2$, $CH_2OCH_3$,

CH₂OC₂H₅, CH₂SCH₃, CH₂SC₂H₅, CH₂SC₆H₅, CH₂NHCOCH₃,

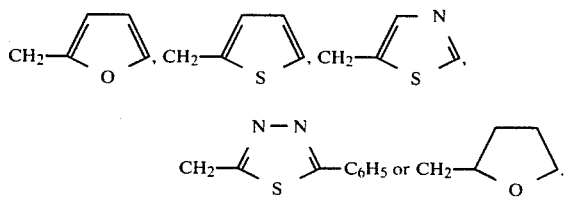

3. The process of claim 1, wherein R is naphthyl or phenyl which is substituted with acetylamino, propionylamino or butyrylamino.

4. The process of claim 1, wherein R is C₆H₅, C₆H₄Cl, C₆H₄Br, C₆H₄CH₃, C₆H₃ClCH₃, C₆H₄NO₂, C₆H₃ClNO₂, C₆H₄OCH₃, C₆H₄OC₂H₅, C₆H₄OC₆H₅, C₆H₃(OCH₃)₂, C₆H₃(CH₃)₂, C₆H₂(OCH₃)₃, C₆H₄N(CH₃)₂, C₆H₄N(C₂H₅)₂, C₆H₄C₄H₉, C₁₀H₇,

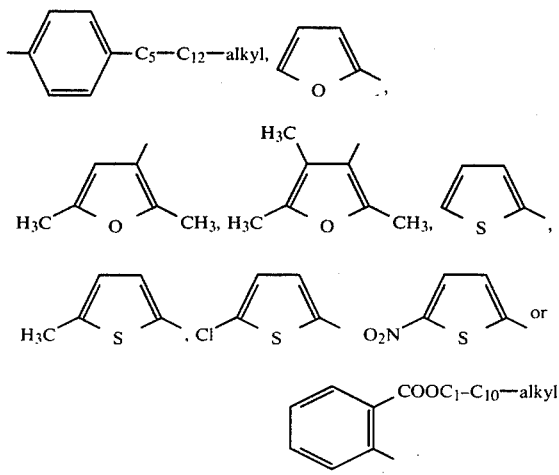

5. The process of claim 1, wherein R¹ and R² are each methyl, ethyl, propyl, butyl, β-hydroxyethyl, β-methoxyethyl, γ-methoxypropyl, β-cyanoethyl, β-carbomethoxyethyl, β-carboethoxyethyl, β-acetoxyethyl, β-ethoxycarbonylethyl, γ-acetylaminopropyl, phenoxycarbonyloxyethyl, butylaminocarbonyloxyethyl, benzyl or β-phenylethyl.

6. The process of claim 1, wherein the compound of formula II is reacted with from an equimolar amount up to about 1.5 molar equivalents of the water-soluble monohaloacetate.

7. The process of claim 1, wherein the compound of formula II is reacted with a water-soluble monohaloacetate in an aqueous alkaline solution for from about 3 to 8 hours.

8. The process of claim 7, wherein the compound of formula II is reacted with the monohaloacetate for from about 4 to 6 hours.

9. The process of claim 1, wherein the compound of formula II is reacted with a monohaloacetate at a temperature of from about 50° to 110° C.

10. The process of claim 9, wherein the temperature is from about 80° to 95° C.

11. The process of claim 1, wherein the monohaloacetate is a sodium salt of a monohaloacetic acid.

12. The process of claim 1, wherein the monohaloacetate is produced in situ from a monohaloacetic acid and a base.

13. The process of claim 1, wherein the compound of formula II is prepared in situ by reacting an acid halide of the formula R—CO—Hal wherein Hal is chlorine or bromine, with an alkali metal thiocyanate or ammonium thiocyanate in a solvent and then adding an amine of the formula $$HN\begin{matrix}R^1\\R^2\end{matrix}$$

wherein R¹ and R² are as defined for formula I.

14. The process of claim 13, wherein Hal is chlorine.

* * * * *